(12) United States Patent
Frank (10) Patent No.: US 7,905,763 B1
(45) Date of Patent: Mar. 15, 2011

(54) MOISTURE MANAGING GARMENT

(75) Inventor: Nanette Frank, San Diego, CA (US)

(73) Assignee: Girlease, LLC, San Diego, CA (US)

( * ) Notice: Subject to any disclaimer, the term of this patent is extended or adjusted under 35 U.S.C. 154(b) by 277 days.

(21) Appl. No.: 12/200,558

(22) Filed: Aug. 28, 2008

Related U.S. Application Data

(60) Provisional application No. 60/969,525, filed on Aug. 31, 2007.

(51) Int. Cl.
*A41C 3/00* (2006.01)
(52) U.S. Cl. .................................. 450/37; 450/81; 450/54
(58) Field of Classification Search ..................... 450/37, 450/54–57, 39, 41; 2/267, 268, 255, 258–260.1, 2/53–56, 46
See application file for complete search history.

(56) References Cited

U.S. PATENT DOCUMENTS

| | | | | |
|---|---|---|---|---|
| 2,728,079 A * | 12/1955 | Williams | .......................... | 450/81 |
| 2,793,369 A * | 5/1957 | Panighini | .......................... | 450/53 |
| 2,869,553 A * | 1/1959 | D'or | .............................. | 450/81 |
| 3,446,213 A * | 5/1969 | Goldman | ......................... | 450/39 |
| 3,934,593 A * | 1/1976 | Mellinger | ........................ | 450/56 |
| 5,603,653 A | 2/1997 | Hartman | | |
| 5,716,255 A * | 2/1998 | Abercrombie et al. | ......... | 450/60 |
| 5,980,359 A * | 11/1999 | Brown | .............................. | 450/57 |
| 5,998,693 A * | 12/1999 | Zagame | ........................... | 602/52 |
| 6,264,530 B1 * | 7/2001 | Cosentino | ........................ | 450/57 |
| 7,001,241 B2 * | 2/2006 | Gorringe et al. | .................. | 450/81 |
| 7,229,335 B2 * | 6/2007 | Davis | .............................. | 450/81 |

OTHER PUBLICATIONS

Ad page- "Pambra's™, the original bra liner that absorbs perspiration under and between the breasts." downloaded off the internet at: http://www.brucemedical.com/paobrali.html on Aug. 13, 2008 (2 copies- 1 copy shows full text of document and 1 copy shows full web address).
Ad page—"Daily Living Aids," R638 Bra Liner, downloaded off the internet at supportplus.com.
"Wick'em Bra Liner: solution for breast rashes caused by sweat", retrieved from the internet at http://www.braliner.com/ on Jun. 23, 2010, 2 pages.
Beauty Boutique®—Bra Liners, retrieved from the internet at http://www.beautyboutique.com/cgi-bin/beauty/cat_item.
html?keywords=022351&media=GB1908&days=XVQ&cm_mmc=Google-_-Non-Brand-_-Bra%20Liners-_-bra%20liners on Jun. 23, 2010, 1 page.

* cited by examiner

*Primary Examiner* — Gloria Hale
(74) *Attorney, Agent, or Firm* — Mandour & Associates, APC (57) ABSTRACT

A garment configured to be worn by a person at the breast fold line, namely where a crease is formed in between the breast under breast area and the chest surface. The garment preferably includes: a body including a flexible sheet of material with an arcuate member having an upwardly curved shape and configured for placement under the breast fold line sized and shaped to extend under a substantial portion of the breast fold line. A first tab is connected to the first arcuate member and extends away from the first arcuate member's top edge. The first tab is connected to the first arcuate member over a distance less than the width of the first tab. The first tab is foldable away form the first arcuate member and connected to the first arcuate member along the top edge close to the first fold line when the garment is worn.

18 Claims, 6 Drawing Sheets

MOISTURE MANAGING GARMENT

CROSS-REFERENCES TO RELATED APPLICATIONS

This application claims the benefit of U.S. Provisional Application Ser. No. 60/969,525 filed Aug. 31, 2007.

BACKGROUND

Persons do many activities and/or have physical characteristics that cause them to sweat. Exercise, natural proclivity to sweat, and skin-on-skin contact can all affect how much and where a person sweats. The sweat a person produces can have many undesired side effects, including staining apparel, producing embarrassing wet spots on clothes, producing rashes and even yeast infections, etc.

Persons have tried various techniques to address the issue and results of undesired skin-on-skin contact. For example, women have put talcum powder and/or tissues under their breasts. Women have also put bra liners, designed to increase bra comfort, under portions of their breasts. This attempted solution, however, has proven inadequate, e.g., due to bunching of the liner, and inadequate inhibition of skin-on-skin contact.

SUMMARY

An exemplary garment according to the disclosure is configured to be worn by a person and includes: a body including a flexible sheet of material having at least a first arcuate member having an upwardly curved shape and being configured to be disposed under a first breast of the person in close proximity to a first fold line of the first breast with a size and shape to extend under a substantial portion of the first fold line; and a first tab connected to the first arcuate member body and extending away from a top edge of the first arcuate member, the first tab being connected to the first arcuate member over a first distance less than a width of the first tab, the first tab being foldable away from the first arcuate member, the first tab being connected to the first arcuate member along the top edge in a region of the top edge that is disposed in close proximity to the first fold line when the garment is worn by the person.

Embodiments of such garments may include one or more of the following features. The body further includes a second arcuate member connected to the first arcuate member and having an upwardly curved shape and being configured to be disposed under a second breast of the person in close proximity to a second fold line of the second breast with a size and shape to extend under a substantial portion of the second fold line, the garment further comprising a second tab connected to the second arcuate member body and extending away from a top edge of the second arcuate member, the second tab being connected to the second arcuate member over a second distance less than a width of the second tab, the second tab being foldable away from the second arcuate member. The first and second tabs extend from approximately middles of the first and second arcuate members respectively. The first and second tabs have curved top edges. The first and second tabs have substantially oval, asymmetric shapes. The first and second tabs extend away from the first and second arcuate members by distances less than a distance from the first and second fold lines to bottoms of the breasts. The first and second tabs extend away from the first and second arcuate members by distances from about 1.25" to about 2.5".

Embodiments of such garments may also, or alternatively, include one or more of the following features. The first and second arcuate members are crescent shaped, with widths near theirs ends being smaller than widths in their middles. The body and the tab include multiple layers of materials including outer layers of soft material, inner layers disposed between the outer layers and comprising liquid-absorbing rayon, and a middle layer disposed between the inner layers and comprising cotton. The garment of claim 1 further comprising an adhesive pad disposed on the tab.

An exemplary undergarment according to the disclosure is configured to be worn by a person under the person's breasts and includes: a body including a thin, flexible material having two crescent-shaped members curving upwardly and sized to be disposed under the person's breasts in close proximity to fold lines of the breasts at junctures between the person's breasts and the person's chest, the crescent-shaped members being sized and shaped to extend under substantial portions of the respective fold lines; and a positioning tab connected to each of the crescent-shaped members and extending away from top edges of the respective crescent-shaped members, each of the tabs being connected to the respective crescent-shaped member over a distance that is less than a width of the tab, the tabs being foldable away from the crescent-shaped members.

Embodiments of such garments may include one or more of the following features. The tabs are disposed approximately in middles of widths of the crescent-shaped members approximately along the top edge in a region of the top edge that is disposed in close proximity to the first fold line when the garment is worn by the person. The positioning tabs have curved top edges. The positioning tabs have substantially oval, asymmetric shapes. The positioning tabs extend away from the crescent-shaped members by distances from about 1.25" to about 2.5". The body and the positioning tabs include multiple layers of materials including outer layers of soft material, inner layers disposed between the outer layers and comprising liquid-absorbing rayon, and a middle layer disposed between the inner layers and comprising cotton. Garments further include an adhesive pad disposed on each of the positioning tabs.

An exemplary undergarment according to the disclosure is configured to be worn by a person under the person's breasts and includes: a body including a thin, flexible sheet having two crescent-shaped members curving upwardly and sized to be disposed under the person's breasts in close proximity to fold lines of the breasts at junctures between the person's breasts and the person's chest, the crescent-shaped members being sized and shaped to extend under substantial portions of the respective fold lines; and means for retaining the body in close proximity to the fold lines, the means for retaining being connected to, but distinct from, the body.

Embodiments of such garments may include one or more of the following features. The flexible sheet comprises multiple layers of different materials. The flexible sheet includes: a top portion comprising multiple layers of polypropylene and a layer of cellulose; a first inner portion having a top surface adjacent a bottom surface of the top portion and including a layer of absorbent, non-woven rayon; a second inner portion having a top surface adjacent a bottom surface of the first inner portion and including a layer of one of (1) cotton or (2) a blend of cotton and poly-cellulose; a third inner portion having a top surface adjacent a bottom surface of the second inner portion and including a layer of absorbent, non-woven rayon; and a bottom portion having a top surface adjacent a bottom surface of the third inner portion and including multiple layers of polypropylene and a layer of cellulose, where the flexible sheet is configured to at least one of wick moisture or provide an air pathway.

Embodiments of the disclosure may provide one or more of the following, and possibly other, capabilities. Excessive buildup of perspiration may be inhibited. Discomfort may be decreased, especially for heavy-set people, people living in hot and/or humid areas, people exercising, women lounging without a bra, menopausal women who are experiencing hot flashes, etc. Evaporation of excess moisture may be increased. Oil removal from skin may be reduced. Conditions such as chafing, rashes, yeast or bacterial infections, itching, etc. may be reduced. Body odor may be reduced. Discoloration and/or staining of clothing such as blouses, shirts, brassieres, pants, shorts, etc. may be reduced. Skin tags may be inhibited/reduced. Skin-on-skin contact may be reduced. Body heat, and/or overheating, including localized overheating, may be reduced. Sweat may be reduced. Ventilation may be increased to certain body parts, e.g., between breast and chest, under arms, etc. Personal comfort and/or confidence may be increased. Milk of nursing women may be inhibited from collecting under the breast. Unhealthy and/or undesirable conditions on or near a woman's breast, including bacteria build up, collection of souring milk, and/or collection of other liquids including perspiration, may be reduced and/or inhibited. A bra liner can help reduce undesired situations and effects while bunching up little if at all. A bra liner can conform to the shape of the breast, cleavage, and chest/rib cage better than previous devices. A garment can be retained in or near a desired location on a person's body well, including better than previous garments. A garment may be comfortably worn, including more comfortably than previous garments.

DETAILED DESCRIPTION

Embodiments of the disclosure provide techniques for reducing and/or accommodating sweat or other liquids at various locations on a person's body. For example, an undergarment may be configured to be disposed between a person's chest and the person's breasts. The undergarment may be made of moisture-absorbing and/or wicking material(s) and shaped to fit comfortably under and in-between the person's breasts. The undergarment can separate the breasts and the chest, inhibit skin-to-skin contact between breast and chest, wick moisture away and/or absorb moisture from a region between breast and chest, and/or provide an air passageway between breast and chest. The undergarment may be shaped to fit under and partially around the breasts to inhibit all or nearly all skin-to-skin contact that normally takes place for a given person. Other embodiments are within the scope of the invention.

Figure 1:
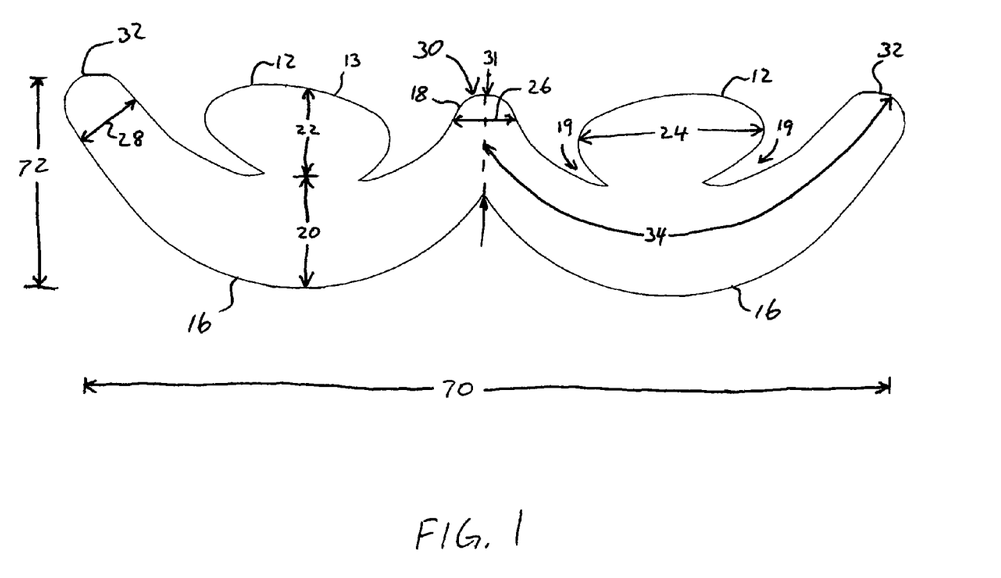
FIG. 1 is a front view of an undergarment for use under a person's breasts.
Figure 2:
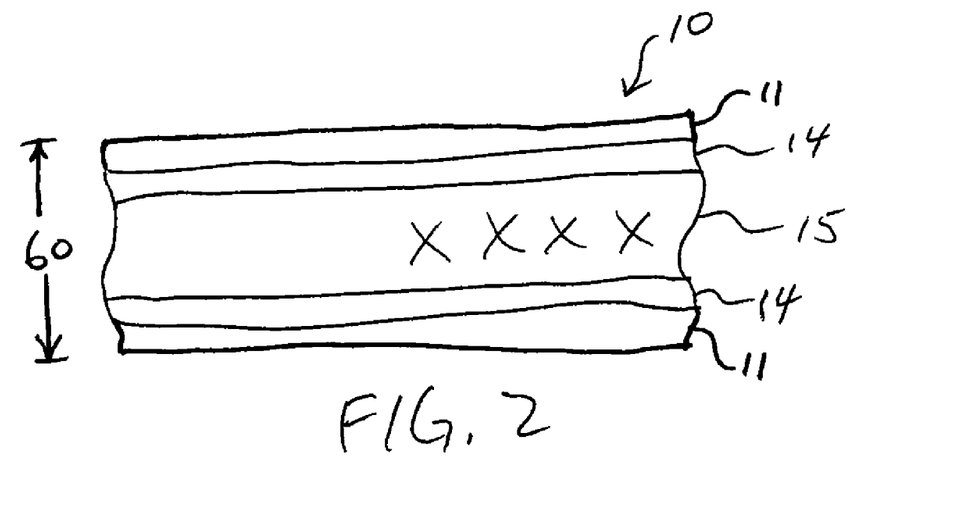
FIG. 2 is a cross-section of a portion of the undergarment shown in FIG. 1.
Figure 3:
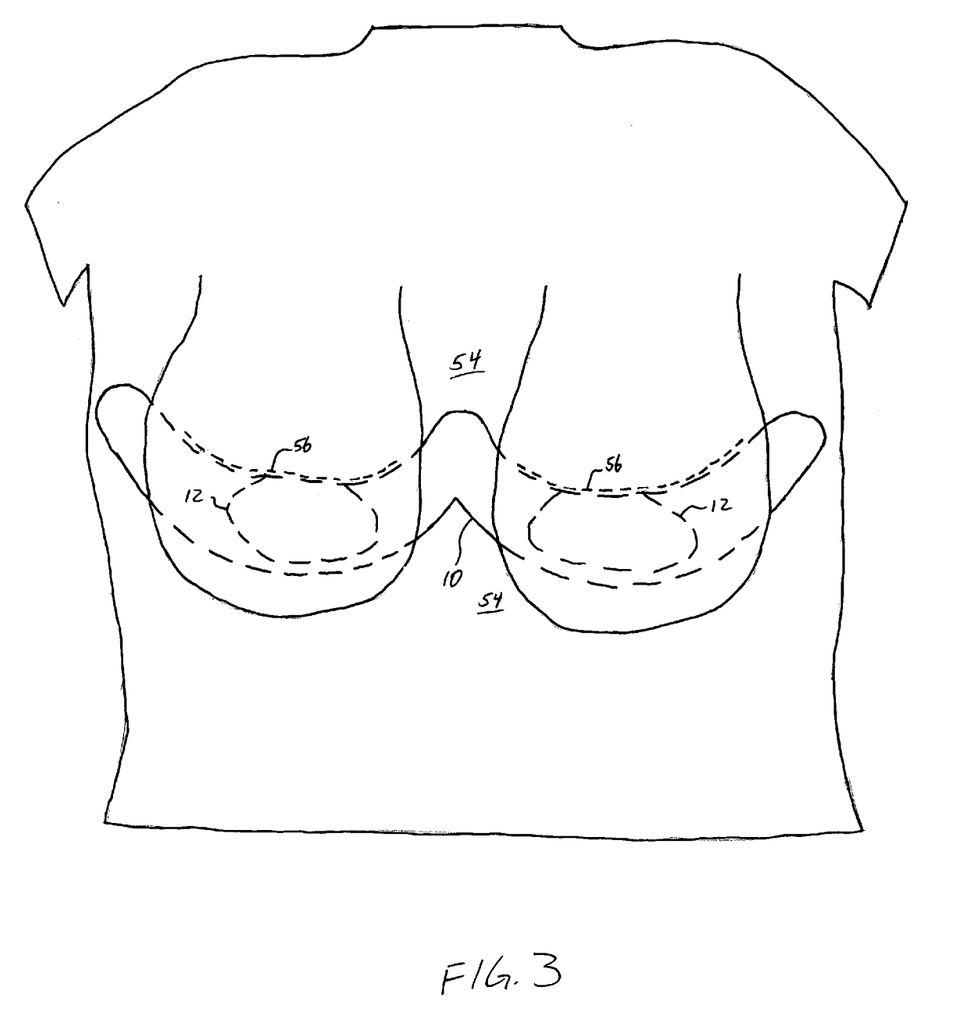
FIG. 3 is a front view of a woman wearing the undergarment shown in FIG. 1, without wearing a brassiere. The phantom lines indicate that the undergarment shown is positioned under the breasts as shown in FIG. 4.
Figure 4:
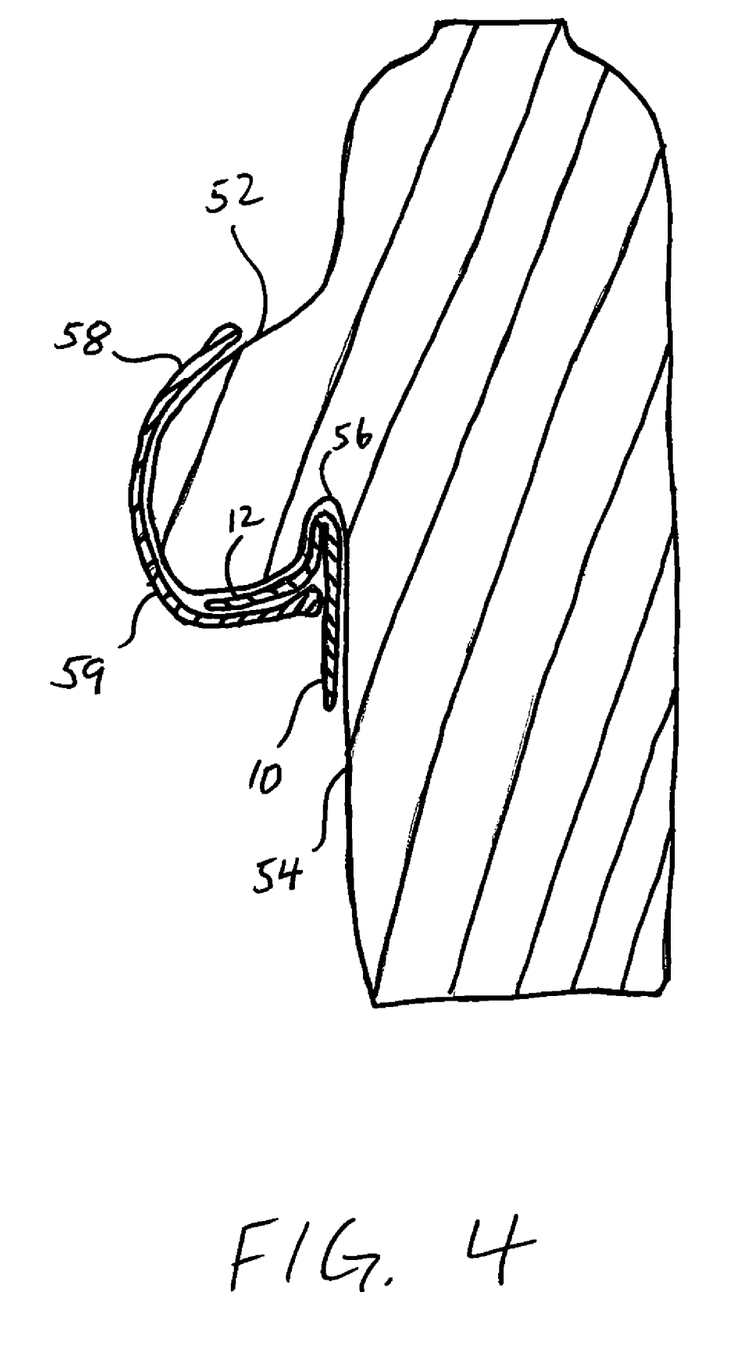
FIG. 4 is a cross-sectional view of a woman wearing the undergarment shown in FIG. 1 while wearing a brassiere.

Referring to FIGS. 1-4, an undergarment 10 is configured to be worn under a person's 50 breasts 52 and to separate the breasts 52 from the person's chest 54. This area of the person's body will be referred to herein as "the breast fold line," namely where a crease is formed in between the breast under-breast area and the chest surface. The breast fold line 56 is shown in FIG. 3 and FIG. 4. The undergarment 10 is made of flexible, disposable or non-disposable, materials and has a dual-crescent shape to conform to and lie under, in between, and around the breasts 52. The undergarment 10 includes tabs 12 and crescent-shaped members 16 configured to be disposed between the breasts 52 and the chest 54, preferably at the breast fold line. The undergarment 10 is preferably hypoallergenic, and may be scented or unscented. The undergarment 10 is configured to be held in place by a brassiere, a clip, adhesive, and/or weight of the breasts 52. Adhesive may be used to attach the undergarment 10 to a brassiere or other clothing or to the person's skin, and/or a clip may be used to attach the undergarment 10 to a brassiere or other clothing.

The two crescent-shaped members 16 extend from a center portion 30 towards tapered ends 32. The tapered ends 32 are preferably rounded, as opposed to being pointed or squared. The members 16 are curved upward when disposed under the breasts 52. The members 16 may have a radial curvature or, as here, a non-radial curvature where the members 16 curve more (tighter) near the center portion 30 and progressively less toward the ends 32 (with the curvature near the ends 32 being less than the curvature near the center portion 30). The amounts of curvature depend on the size of the undergarment and corresponding breast size. The members 16 are sized and shaped to fit under the breasts 52 along breast fold lines 56 at breast-chest junctures (where breast-to-chest skin-to-skin contact occurs if not inhibited), and to be disposed in close proximity to the fold lines 56 for substantially entire lengths of the fold lines 56. The distance 34 is preferably long enough such that the members 16 extend at least under a substantial portion of, and more preferably nearly completely, and even more preferably completely, under the breast-chest fold lines 56 yet do not extend outwardly significantly beyond the fold line 56 or beyond the breasts 52 so that the ends 32 are covered by a bra 59 (FIG. 4) and/or do not produce a visible ridge or step through the wearer's clothing.

The breast tabs 12 are configured to help position the garment 10 and to inhibit movement of the garment 10 while worn. With the garment 10 laid flat, the tabs 12 extend upward from the crescent members 16 approximately in the middle of the members 16. The tabs 12 have an oblong shape and are mirror images of each other. The tabs 12 may be symmetrical or, as here, slightly asymmetrical, extending further from the crescent members 16 toward the respective ends 32 than toward the center portion 30. The tabs 12 are configured to be disposed inside a lower portion of a cup 58 of the bra 59, with the underside of the breasts 52 resting on the tabs 12. The tabs 12 conform to the curvature underside of the breasts 52, above the fold line 56, and are small enough so as not to come up from underneath the breasts 52 to avoid showing through a thin shirt. The tabs 12 are bendable relative to the members 16 such that the tabs 16 can be folded away from the members 16 and disposed between bra cups 58 (one shown in FIG. 4) of the bra 59 and the breasts 52 as shown in FIG. 4. In use, the weight of the breasts 52 against the tabs 12 helps to hold the garment 10 in place. The tabs 12 are shaped to be disposed on the under side of the breasts 52 during use. Heights 22 of the tabs 12 are such that the tabs 12 provide sufficient friction against the bra 59 under weight of the breasts 52 to hold the garment 10 substantially stationary while in use. The tabs 12 have curved edges 13 to fit to curvatures of undersides of the breasts 52, above the breast-to-chest fold line area. Heights 22 of the tabs 12 are such that the tabs 12 can help prevent movement of the garment 10 while in use, yet not extend beyond undersides of the breasts, such that any ridge or step produced by the edges 13 are not visible in a front view of a person wearing the garment 10. Further, the tabs 12 are connected to the members 16 over distances 17 (e.g., about two inches) that less than their widths 24, providing undercut regions 19.

Referring specifically to FIG. 2, the undergarment 10 includes multiple layers 11, 14, 15 of materials providing a thin sheet that is the undergarment 10. Each layer 11, 14, 15 may comprise multiple layers itself. The materials of the layers 11, 14, 15 preferably are flexible and make the garment 10 absorbent and moisture-retaining, and such that the garment may be disposable or more durable/washable/reusable. The garment 10 is preferably reversible and symmetric such that either layer 14 may be placed against the user's chest 54. The garment 10 preferably has a combined thickness 60 of about ⅛ of an inch, although other thicknesses may be used, e.g., thicker garments for use in extremely hot and/or humid conditions. The garment 10 is configured to wick away moisture from, and to provide an air pathway, underneath, in between, and around the breasts. The garment 10 comprises air-laid, non-woven, hygienic, hypo-allergenic, material such as cotton, silk, etc. The outer layers 11 are soft to touch and quilted for air flow. The layers 11 are preferably multi-layer composites of two or more layers of polypropylene and one or more layers of cellulose. For example, model 7408 made by Lymtech Scientific, a Division of the John R. Lyman Company of Chicopee, Mass. may be used for the cellulose layer (s). The inner layers 14 each comprise one or more layers of nonwoven, (super) absorbent Rayon, such as model XL 7400 made by Lymtech Scientific. The middle layer 15 may comprise cotton (e.g., 100% cotton) a or cotton/poly-cellulose blend, or other moisture-retaining material and/or a stabilizing, breathable material. Materials of the layers 11, 14, 15 may vary depending on desired absorbency. The materials making up the garment 10 may be similar to a feminine hygiene pad or other article (e.g., panty liner, diaper, incontinence garment) but double-sided instead of one sided and comprising a plastic outer liner.

The layers 11, 14, 15 are connected to inhibit slippage relative to each other while allowing wicking and/or air flow. Here, the layers 11, 14, 15 are bonded together and further sonically spot bonded in a quilt-like manner such that the garment 10 is embossed, allowing air flow. The outside edges of the undergarment 10 may stitched, heated and adhered, etc. Alternatively, the layers 11, 14, 15 may be joined by being sewn together with or without being bonded. Additional layers and material types may be used, e.g., depending upon the temperature in which the garment will be worn.

The undergarment 10 may also be embossed for additional stabilization, comfort, absorbency, moisture retention, decoration, etc., and may have decorative trim, and or cut shapes around the edges, and powder, ointment, or cream; i.e. aloe, anti-itch, etc. The undergarment 10 may be individually wrapped.

Size may vary for the undergarment 10 to accommodate different persons, e.g., of different sizes, shapes, etc. For example, the undergarment may be made of different sizes to accommodate different brassiere sizes: a, b, c, d, dd, e, f, etc. For different chest and/or breast sizes, the garment 10 including the tabs 12 will preferably vary accordingly. For example, for brassiere size of 38-C, the following dimensions are preferred: a height 20 of the central portion 30 of the tapered crescent members 16 of about 1.75", the heights 22 of the breast tabs 12 of from about 1.25" to about 1.75", the widths 24 of the breast tabs 12 of about 4", a width 26 of a center member 18 of about 2", a height 31 of the center member 18 of about 1.75", a width 28 near ends of the tapered crescent members 16 of about 1.25", and a distance 34 from the center of the garment 10 to one end 32 of about 12". For a garment for a 38-D bra size, the distance 34 would preferably be about 12" and for a bra size of 32-F would preferably be about 9". Here, the garment 10 has a width 70 of about 17.6 inches and a height 72 of about 4.4 inches and would preferably be used with bra sizes of 32-F to 44-D. For a 44-D bra size, the following dimensions are preferred: the distance 34 of about 14", the width 24 of from about 4.5" to about 5", the height 20 of about 2.5", the height 31 of about 2.5", the width 18 of about 3 inches, the tab height 22 of about 2.5", and the width 28 of from about 1.75" to about 2".

The garment 10 can be easily fit to a person's body to help prevent skin-to-skin contact. The user folds the tabs 12 away from the members 16 (e.g., tilting slightly upward) and places the tabs 12 under the breasts 52 and inside the underside of the brassiere cups 58, with the members 12 near the breast-to-chest fold lines 56. The user dons the bra 59, putting the bra cups 58 between the tabs 12 and the members 16 as shown in FIG. 4. The weight of the breasts 52 against the tabs 12 helps to hold the garment 10 in place. As shown in FIG. 4, the bra 59 sits below the top edge of the garment 10, e.g., about one half of an inch or about midway along the height of the members 16.

Figure 5:
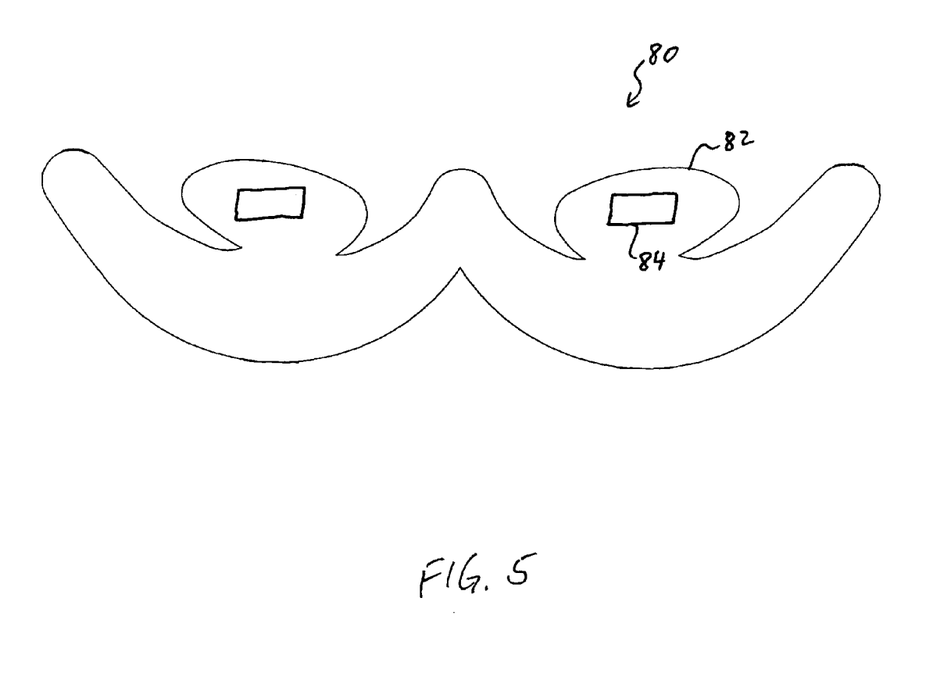
FIG. 5 is a front view of an alternative embodiment of the undergarment for use under a person's breasts.
Figure 6:
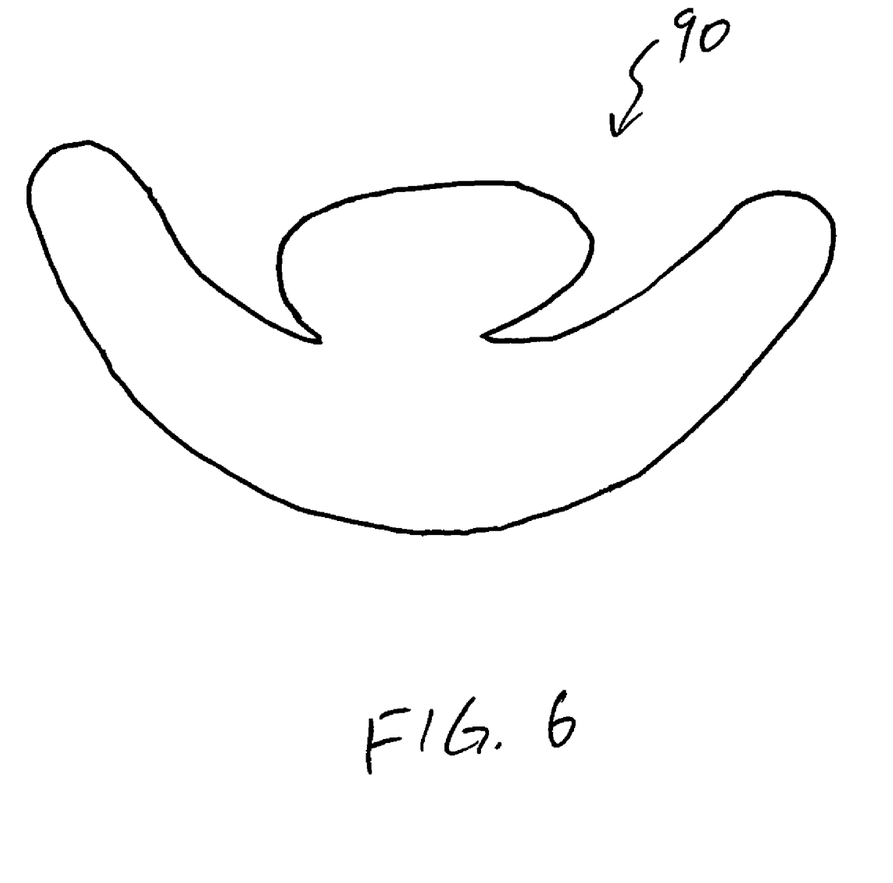
FIG. 6 is a front view of another alternative embodiment of the undergarment for use under a person's breast.

Other embodiments are within the scope of the invention. While the description above focused on avoiding skin-to-skin contact between breast and chest, the undergarment may be used to avoid skin-to-skin contact between breast and stomach as well, although in the latter case, a larger-height undergarment may be desired, e.g., with the height 20 being larger (e.g., twice as large, about 4, 5, or 6 inches, etc.) than for undergarments when contact with the stomach is not an issue. Further, undergarments according to the disclosure may be used for many different areas of a person's body, e.g., the back, the stomach, the underarm, the anal cleft, the lower back, etc. Undergarments for use with breasts may not include breast tabs. Further, undergarments may be made to custom fit the individual, versus being mass produced. Further still, the embodiments of the invention may be designed (e.g., shaped, sized, etc.) for other portions of a person's body, e.g., the neck (e.g., to prevent staining collars), the upper or lower back, the stomach, the underarms, the anal cleft, etc. Also, while the disclosure focused on undergarments, items in accordance with the disclosure need not be undergarments, i.e., worn under other garments. Further, other shapes than those described may be used, e.g., with portions disposed under the breasts not tapering. Also, as shown in FIG. 5, an alternative garment 80 has tabs 82 that include adhesive pads 84 covered with peal-away sheets to be removed before use. The pads 84 are configured to adhere the garment 80 to insides of the bra cups 58 (see FIG. 4) to help retain the garment 80 in place during use. Additionally, or alternatively, adhesive pads may be placed at other locations on the garment. Alternatively, other mechanisms may be used to help retain the garment in position, e.g., clips. Alternatively still, referring to FIG. 6, a single-member garment 90, e.g., approximately one half of the garment 10 (or other embodiment) is configured for use under a single breast.

Still other embodiments are within the scope of the invention. For example, garments may have substances, e.g., antiyeast infection medication, disposed on or in the garment. Other substances may be used, such as talc, materials for absorbing liquid, perfumes, deodorants, anti-fungal medication, anti-perspirant (e.g., aluminum chloride, aluminum zirconium tricholorohydrex glycine, aluminum chlorohydrate, aluminym hydroxybromide), etc. Further, other tab heights 22 may be used, e.g., about three-quarters of an inch, about one inch, about one and a half inches, about one and three quarters inches, about two inches, etc. Further still, garments according to the description may be provided in various colors, e.g., white, beige, pink, etc.

What is claimed is:

1. A garment configured to be worn by a person, the garment comprising:
    a body comprising a flexible sheet of material having at least a first arcuate member having an upwardly curved shape and being configured to be disposed under a first breast of the person in close proximity to a first breast fold line of the first breast with a size and shape to extend under a substantial portion of the first breast fold line; and,
    a first tab connected to the first arcuate member body and extending away from a top edge of the first arcuate member, the first tab being connected to the first arcuate member at the top edge over a first distance less than a width of the first tab, the first tab being foldable away from the first arcuate member, the first tab being connected to the first arcuate member along the top edge in a region of the top edge that is disposed in close proximity to the first breast fold line and does not extend above the undersides of the breast when the garment is worn by the person.

2. The garment of claim 1 wherein the body further comprises a second arcuate member connected to the first arcuate member and having an upwardly curved shape and being configured to be disposed under a second breast of the person in close proximity to a second breast fold line of the second breast with a size and shape to extend under a substantial portion of the second breast fold line, the garment further comprising a second tab connected to the second arcuate member body and extending away from a top edge of the second arcuate member, the second tab being connected to the second arcuate member over a second distance less than a width of the second tab, the second tab being foldable away from the second arcuate member.

3. The garment of claim 2 wherein the first and second tabs extend from approximately middles of the first and second arcuate members respectively.

4. The garment of claim 2 wherein the first and second tabs have curved top edges.

5. The garment of claim 4 wherein the first and second tabs have substantially oval, asymmetric shapes.

6. The garment of claim 4 wherein the first and second tabs extend away from the first and second arcuate members by distances from about 1.25" to about 2.5".

7. The garment of claim 1 wherein the first and second arcuate members are crescent shaped, with ends having a width and said widths near theirs ends being smaller than widths in their middles.

8. A garment configured to be worn by a person, the garment comprising:
    a body comprising a flexible sheet of material having at least a first arcuate member having an upwardly curved shape and being configured to be disposed under a first breast of the person in close proximity to a first breast fold line of the first breast with a size and shape to extend under a substantial portion of the first breast fold line; and,
    a first tab connected to the first arcuate member body and extending away from a top edge of the first arcuate member, the first tab being connected to the first arcuate member over a first distance less than a width of the first tab, the first tab being foldable away from the first arcuate member, the first tab being connected to the first arcuate member along the top edge in a region of the top edge that is disposed in close proximity to the first breast fold line when the garment is worn by the person
    wherein the first arcuate member body and the first tab comprise at least two outer layers of soft material, at least two inner layers disposed between the outer layers and comprising liquid-absorbing rayon, and a middle layer disposed between the inner layers and comprising cotton.

9. The garment of claim 1 further comprising an adhesive pad disposed on the tab.

10. An undergarment configured to be worn by a person under the person's breasts, the undergarment comprising:
    a body comprising a thin, flexible material having two connected crescent-shaped members curving upwardly and sized to be disposed under the person's breasts in close proximity to breast fold lines at junctures between the person's breasts and the person's chest, the crescent-shaped members being sized and shaped to extend under substantial portions of the respective breast fold lines; and
    a positioning tab connected to each of the crescent-shaped members and extending away from top edges of the respective crescent-shaped members, each of the tabs being connected to the respective crescent-shaped member over a distance that is less than a width of the tab, the tabs being foldable away from the crescent-shaped members.

11. The undergarment of claim 10 wherein the positioning tabs have curved top edges.

12. The undergarment of claim 11 wherein the positioning tabs have substantially oval, asymmetric shapes.

13. The undergarment of claim 10 wherein the positioning tabs extend away from the crescent-shaped members by distances from about 1.25" to about 2.5".

14. An undergarment configured to be worn by a person under the person's breasts, the undergarment comprising:
    a body comprising a thin, flexible material having two crescent-shaped members curving upwardly and sized to be disposed under the person's breasts in close proximity to breast fold lines at junctures between the person's breasts and the person's chest, the crescent-shaped members being sized and shaped to extend under substantial portions of the respective breast fold lines; and
    a positioning tab connected to each of the crescent-shaped members and extending away from top edges of the respective crescent-shaped members, each of the tabs being connected to the respective crescent-shaped member over a distance that is less than a width of the tab, the tabs being foldable away from the crescent-shaped members;
    wherein the body and the positioning tabs comprise at least five layers of materials including at least two outer layers of soft material, at least two inner layers disposed between the outer layers and comprising liquid-absorbing rayon, and a middle layer disposed between the inner layers and comprising cotton.

15. The undergarment of claim 10 further comprising an adhesive pad disposed on each of the positioning tabs.

16. An undergarment configured to be worn by a person under the person's breasts, the undergarment comprising:
    a body comprising a thin, flexible sheet having two crescent-shaped members curving upwardly and sized to be disposed under the person's breasts in close proximity to breast fold lines at junctures between the person's breasts and the person's chest, the crescent-shaped members being sized and shaped to extend under substantial portions of the respective breast fold lines; and
    means for retaining the body in close proximity to the breast fold lines, the means for retaining being connected to, but distinct from, the body.

17. The undergarment of claim 16 wherein the flexible sheet comprises multiple layers of different materials.

18. An undergarment configured to be worn by a person under the person's breasts, the undergarment comprising:
    a body comprising a thin, flexible sheet having two crescent-shaped members curving upwardly and sized to be disposed under the person's breasts in close proximity to breast fold lines at junctures between the person's breasts and the person's chest, the crescent-shaped members being sized and shaped to extend under substantial portions of the respective breast fold lines; and
    means for retaining the body in close proximity to the breast fold lines, the means for retaining being connected to, but distinct from, the body;
    wherein the flexible sheet further comprises:
    a top portion comprising multiple layers of polypropylene and a layer of cellulose;
    a first inner portion having a top surface adjacent a bottom surface of the top portion and comprising a layer of absorbent, non-woven rayon;
    a second inner portion having a top surface adjacent a bottom surface of the first inner portion and comprising a layer of one of (1) cotton or (2) a blend of cotton and poly-cellulose;
    a third inner portion having a top surface adjacent a bottom surface of the second inner portion and comprising a layer of absorbent, non-woven rayon; and, a bottom portion having a top surface adjacent a bottom surface of the third inner portion and comprising multiple layers of polypropylene and a layer of cellulose;
    wherein the flexible sheet is configured to at least one of wick moisture or provide an air pathway.

* * * * *